US010398630B2

(12) United States Patent
Azzolini et al.

(10) Patent No.: US 10,398,630 B2
(45) Date of Patent: Sep. 3, 2019

(54) APPLIANCE FOR ENTERAL NUTRITION

(71) Applicant: SIDAM S.r.l., Frazione San Giacomo Roncole (IT)

(72) Inventors: Graziano Azzolini, Cavezzo (IT); Francesco Mojoli, Frazione San Giacomo Roncole (IT); Andrea Tromba, Frazione San Giacomo Roncole (IT)

(73) Assignee: SIDAM S.r.l., Mirandola (MO) (IT)

( * ) Notice: Subject to any disclaimer, the term of this patent is extended or adjusted under 35 U.S.C. 154(b) by 175 days.

(21) Appl. No.: 15/513,565

(22) PCT Filed: Sep. 17, 2015

(86) PCT No.: PCT/IB2015/057169
§ 371 (c)(1),
(2) Date: Mar. 23, 2017

(87) PCT Pub. No.: WO2016/046707
PCT Pub. Date: Mar. 31, 2016

(65) Prior Publication Data
US 2017/0304154 A1     Oct. 26, 2017

(30) Foreign Application Priority Data

Sep. 23, 2014   (IT) .............................. MO2014A0273

(51) Int. Cl.
*A61J 15/00*     (2006.01)
*A61B 5/00*     (2006.01)
(Continued)

(52) U.S. Cl.
CPC ........... *A61J 15/0084* (2015.05); *A61B 5/037* (2013.01); *A61B 5/08* (2013.01); *A61B 5/6853* (2013.01);
(Continued)

(58) Field of Classification Search
CPC .. A61J 15/0084; A61J 15/0015; A61J 15/008; A61J 15/0049; A61M 16/026; A61M 16/0415; A61B 5/037; A61B 5/08
See application file for complete search history.

(56) References Cited

U.S. PATENT DOCUMENTS

| 5,321,392 A | * | 6/1994 | Skakoon | ........... | A61M 5/16831 |
| | | | | | 320/106 |
| 2001/0053920 A1 | * | 12/2001 | Shaker | .................... | A61B 5/037 |
| | | | | | 606/197 |

(Continued)

FOREIGN PATENT DOCUMENTS

IT         MO20110133         11/2012

OTHER PUBLICATIONS

International Search Report and the Written Opinion dated Jan. 22, 2016 From the International Searching Authority Re. Application No. PCT/IB2015/057169. (13 Pages).

(Continued)

*Primary Examiner* — Bradley J Osinski

(57) ABSTRACT

An appliance (1) for enteral nutrition by means of a probe of the type comprising a tubular element of elongated shape and substantially flexible which defines a feeding channel open at the extremities for the introduction of nutritional substances in the stomach of a patient and which comprises at least a first inflatable balloon for detecting the pressure inside the esophagus of a patient, the tubular element comprising at least a first inlet/outlet mouth for the air in/from the first balloon, the appliance (1) further comprising:

at least a pneumatic circuit (3) having pumping means (4) associable at least with the first inlet/outlet mouth for inflating/deflating the first balloon;

(Continued)

processing means (8) comprising:
  detection means which can be connected to the first balloon to detect the patient's oesophageal pressure ($p_{es}$);
  reading means of the pressure of the respiratory tract ($p_{aw}$) which can be connected to an external detection device;
  calculation means operatively connected to the detection means and to the reading means and able to calculate at least the transpulmonary pressure ($p_{tp}$);
graphic display means (10) operatively connected to the processing means (8) and able to display at least one of the oesophageal pressure ($p_{es}$), the pressure of the respiratory tract ($p_{aw}$) and the transpulmonary pressure ($p_{tp}$).

14 Claims, 2 Drawing Sheets

(51) Int. Cl.
  *A61B 5/03* (2006.01)
  *A61B 5/08* (2006.01)
  *A61M 16/04* (2006.01)
  *A61M 16/00* (2006.01)
(52) U.S. Cl.
  CPC .............. *A61B 5/742* (2013.01); *A61J 15/008* (2015.05); *A61J 15/0015* (2013.01); *A61J 15/0049* (2013.01); *A61J 15/0073* (2013.01); *A61J 15/0076* (2015.05); *A61M 16/026* (2017.08); *A61M 16/044* (2013.01); *A61M 16/0415* (2014.02); *A61B 2560/0214* (2013.01); *A61M 2016/0027* (2013.01); *A61M 2205/3344* (2013.01); *A61M 2205/505* (2013.01); *A61M 2205/8206* (2013.01)

(56) References Cited

U.S. PATENT DOCUMENTS

| 2008/0121231 | A1* | 5/2008 | Sinderby | A61B 5/037 128/204.21 |
|---|---|---|---|---|
| 2008/0154191 | A1 | 6/2008 | Gobel | |
| 2010/0228142 | A1 | 9/2010 | Sinderby | |
| 2013/0218106 | A1* | 8/2013 | Coston | A61B 5/207 604/317 |

OTHER PUBLICATIONS

Chiumello et al. "A Validation Study of a New Nasogastric Polyfunctional Catheter", Intensive Care Medicine, XP019894793, 37(5): 791-795, Published Online Mar. 2, 2011.

Chiumello et al. "Lung Stress and Strain During Mechanical Ventilation for Acute Respiratory Distress Syndrome", American Journal of Rspiratory and Critical Care Medicine, XP055015837. 178(4): 346-355, Published Online May 1, 2008.

* cited by examiner

APPLIANCE FOR ENTERAL NUTRITION

RELATED APPLICATIONS

This application is a National Phase of PCT Patent Application No. PCT/IB2015/057169 having International filing date of Sep. 17, 2015, which claims the benefit of priority of Italian Patent Application No. MO2014A000273 filed on Sep. 23, 2014. The contents of the above applications are all incorporated by reference as if fully set forth herein in their entirety.

FIELD AND BACKGROUND OF THE INVENTION

The present invention relates to an appliance for enteral nutrition.

In the medical field, so-called enteral nutrition is known of patients who must necessarily be fed artificially.

In medical practice, to perform such nutrition gastric probes of different types are used, classified by location site and type of use.

Nasogastric probes, e.g., are able to be introduced into a nostril of the nose, through the throat and the oesophagus, until they reach the patient's stomach.

Known probes generally comprise a tubular element made of soft and flexible material, of the silicone or polyurethane type, with variable section and length according to the type of application and the age of the patient.

The distal extremity of the tubular element can be positioned inside the stomach of a patient and is commonly provided with a plurality of holes for dispensing the nutritive substances.

The proximal extremity of the tubular element is provided with a feeding mouth for the nutritive substances, which can be administered both by gravity and by means of positive-displacement pumps.

Enteral nutrition is also known to be performed on artificially ventilated patients, e.g. in the case in which the normal vital functions of a patient are compromised or altered as a result of an acute disease or a traumatic event.

Consequently, it is necessary to probe the pressure at several points along the tube, in order to adequately regulate the assisted ventilation of the patient.

To obviate this need, probes are known for enteral nutrition provided with a balloon made of an inelastic material which is arranged at a section of the tubular element and which is connected to a suitable transducer able to determine the pressure present outside the balloon itself.

These known probes have however a number of drawbacks.

In particular, the known probes allow the detection of the pressure at just one point along the tubular element, thus considerably limiting the quality of patient monitoring and, therefore, the possibility of appropriate interventions to regulate the assisted ventilation.

Such drawback has been overcome through the use of a probe with two inflatable balloons spaced apart the one from the other, able to detect the pressure inside the patient's digestive system at two separate sections of the relative tubular element. These probes of known type, whether provided with one or two inflatable balloons, do have several drawbacks.

These in fact are complicated for medical personnel to use.

More particularly, the use of such probes requires the performance of a high number of phases for the detection of various parameters of interest and, therefore, long performance times.

It follows that the use of the probes of known type proves to be considerably inconvenient from the point of view of the time required for their use and, therefore, also in economic terms, due to the exploitation of health personnel and medical hospital facilities.

SUMMARY OF THE INVENTION

The main aim of the present invention is to provide an appliance that allows to simplify the use of the probes of known type by the medical staff.

Within this aim, one object of the present invention is to reduce significantly the time needed for their use.

Another object of the present invention is to reduce the health care costs related to the use of the probes of known type.

Another object of the present invention is to provide an appliance for enteral nutrition which allows to overcome the mentioned drawbacks of the prior art within the ambit of a simple, rational, easy, effective to use as well as low cost solution.

The objects stated above are achieved by the present appliance for enteral nutrition according to claim 1.

BRIEF DESCRIPTION OF THE SEVERAL VIEWS OF THE DRAWINGS

Other characteristics and advantages of the present invention will become better evident from the description of a preferred yet not exclusive embodiment of an appliance for enteral nutrition, illustrated by way of an indicative, but non-limiting, example in the accompanying drawings in which.

DESCRIPTION OF SPECIFIC EMBODIMENTS OF THE INVENTION

Figure 1:
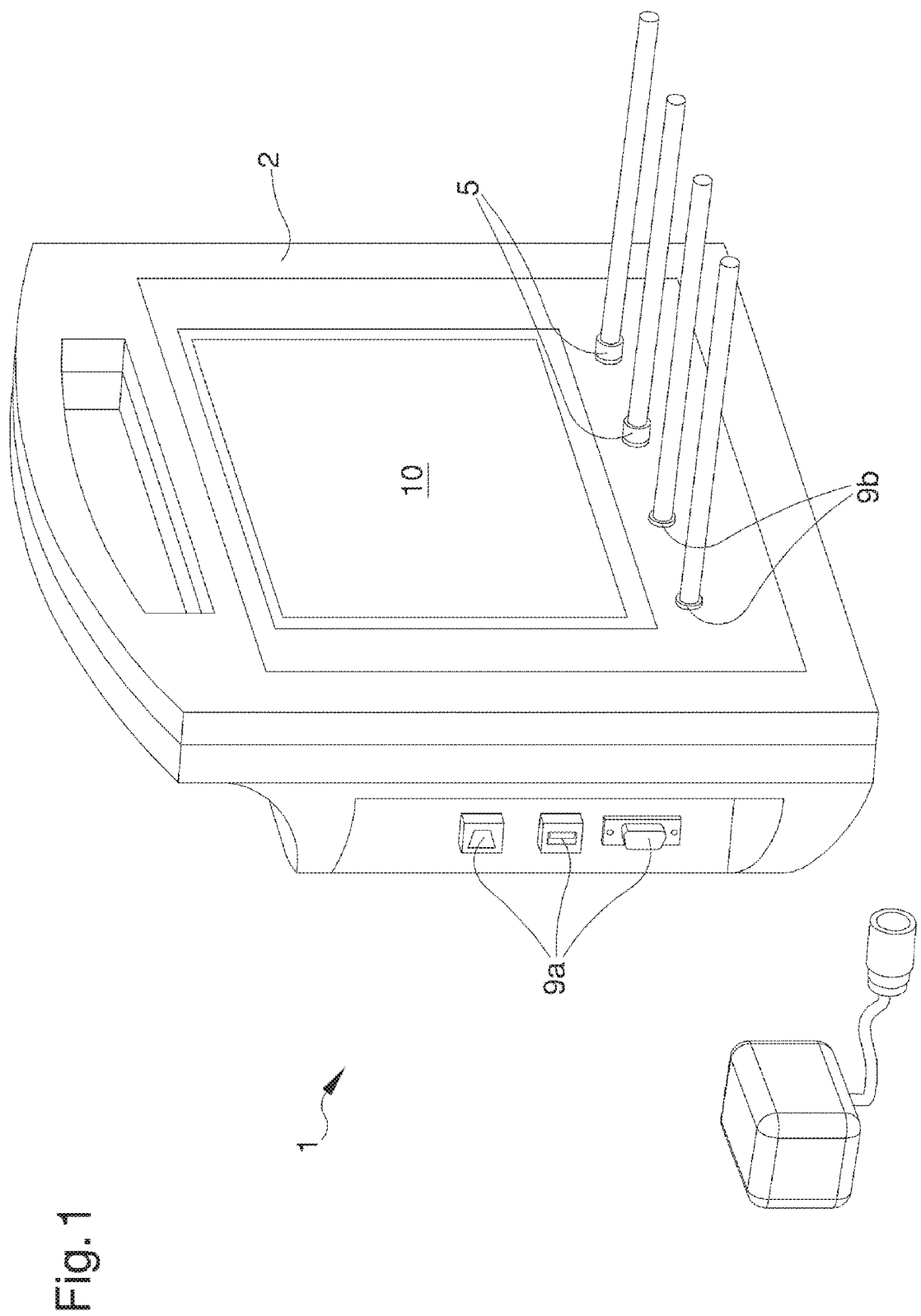
FIG. 1 is an axonometric view of an appliance according to the invention.
Figure 2:
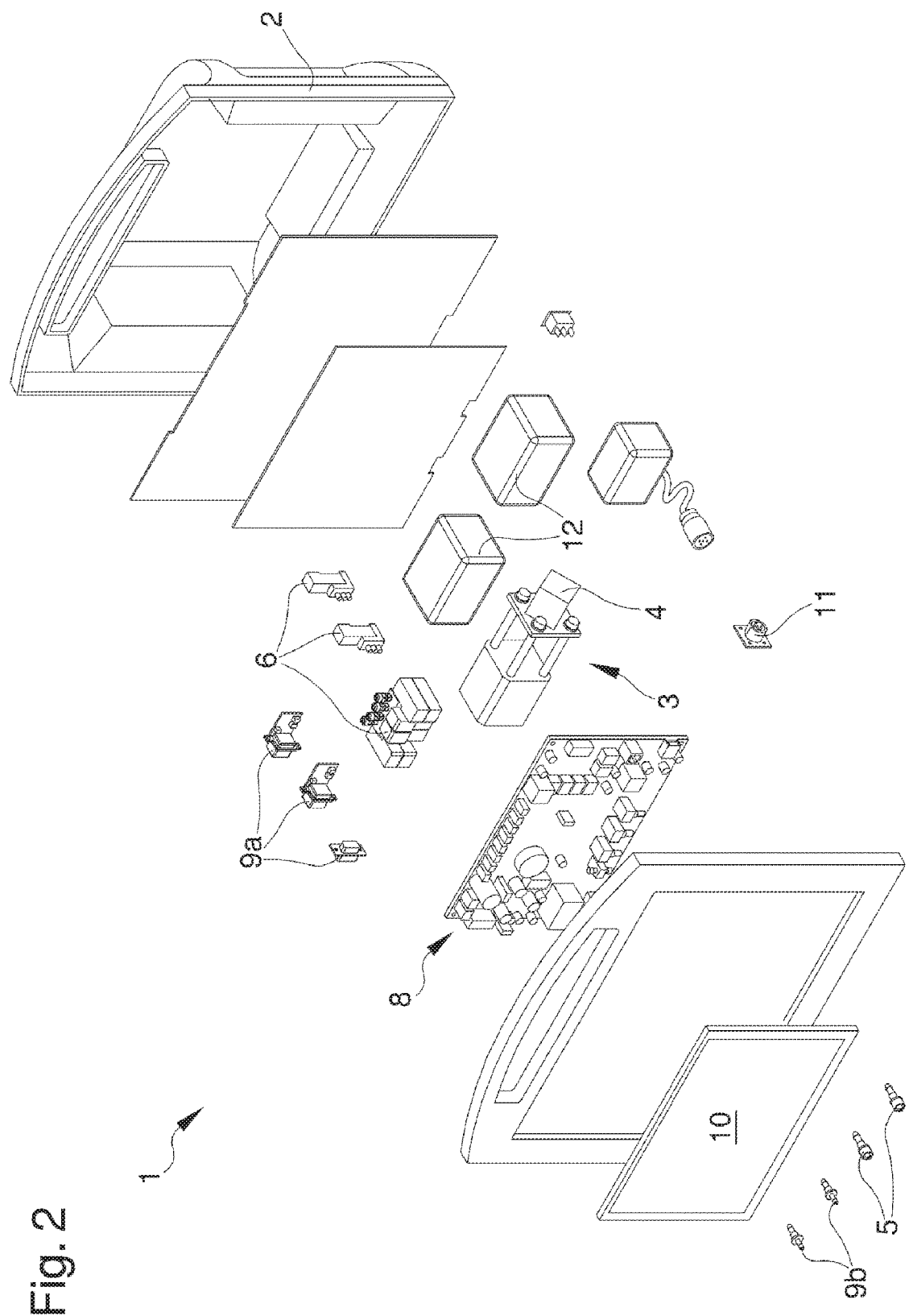
FIG. 2 is an exploded view of the appliance of FIG. 1.

With particular reference to such figures, reference number 1 globally indicates an appliance for enteral nutrition by means of a probe of the type comprising a tubular element of elongated shape and substantially flexible which defines a feeding channel open at the extremities for the introduction of nutritional substances or drugs in the stomach of a patient or the aspiration of fluids from same.

The probes used, not shown in the enclosed illustrations, may be of two types.

The first type envisages the presence of a first inflatable balloon for detecting the pressure inside the patient's oesophagus, where the tubular element comprises at least a first air inlet/outlet mouth in/from the first balloon.

The second type envisages the presence of a first and a second inflatable balloon for detecting the patient's oesophageal and gastric pressure, where the tubular element comprises a first and a second air inlet/outlet mouth in/from the first and second balloon respectively.

The description is now given of an embodiment of the appliance for enteral nutrition with a probe according to the first type referred to above.

The appliance 1 comprises a box-shaped body 2 inside which is arranged, according to the invention, at least one pneumatic circuit 3 having pumping means 4 associated with the first air inlet/outlet mouth for the inflation/deflation of the first balloon.

According to the invention, the pumping means 4 are the type of a syringe pump, which is characterized by positive displacement behaviour, which allows direct linearity between the electrical commands and the insufflated or aspirated volume, and by its air tightness irrespective of the pressure present in the relevant balloon.

More in detail, the syringe pump 4 is commanded by an actuator with a worm screw.

More particularly, the pneumatic circuit 3 comprises at least an air flow duct, not shown in detail in the illustrations, connected to the pumping means 4 and having at least an air inlet/outlet gap 5, e.g. having a connection of the Luer-lock type, associable with the first air inlet/outlet mouth for the inflation/deflation of the first balloon, in order to check its seal. The pneumatic circuit 3 also comprises one or more controllable solenoid valves 6 to allow/prevent the movement of air along the flow duct.

Conveniently, the appliance 1 also comprises at least air outlet means, able to allow air to come out from the balloons.

According to the invention, the appliance 1 comprises processing means 8 having at least detection means which can be connected at inlet at least to the first balloon to detect at least the patient's oesophageal pressure $p_{es}$.

Preferably, the processing means 8 are operatively connected to at least one between the pumping means 4 and the outlet means to command their start/stop.

Advantageously, the detection means comprise at least a first transducer device of the pressure detected outside the first balloon and means for receiving such detected pressure. In the event of the probe having one or more transducer devices, the detection means only comprise pressure receiving means having an electrical connection to the transducer of the probe.

The processing means 8 then comprise reading means of the pressure of the patient's respiratory tract $p_{aw}$ which can be connected at inlet to a detection device such as, e.g., a fan used for the forced ventilation of the patient or a flow sensor. Preferably, said reading means comprise at least one port 9a, 9b for the connection to the external detection device. More in detail, the reading means comprise at least one port 9a for the serial or parallel connection to an external ventilation device and/or at least one port 9b for the connection to an external flow sensor.

More in detail, the appliance 1 also comprises at least one port 9a of the type of an Ethernet port, through which it is possible to communicate with the hospital information system to remotely monitor the data provided by the appliance itself in real time.

According to the invention again, the appliance 1 comprises calculation means operatively connected at inlet to the detection means and to the reading means and able to calculate at least the transpulmonary pressure $p_{tp}$ corresponding to the difference between the pressure of the respiratory tract $p_{aw}$ read and the oesophageal pressure $p_{es}$ detected in a particular moment.

Advantageously, the calculation means are able to calculate the variation in transpulmonary pressure $\Delta p_{tp}$ in two different moments, i.e. the difference between the transpulmonary pressure $p_{tp}$ calculated in a first moment t1 and in a second moment t2:

$$\Delta p_{tpC}=p_{tp}(t1)-p_{tp}(t2)=(p_{aw}(t1)-p_{es}(t1))-(p_{aw}(t2)-p_{es}(t2))$$

The moments t1 and t2 may e.g. correspond to the moments of beginning and end of inhalation/exhalation.

Conveniently, the processing means comprise at least a first programmable memory with at least one of a reference interval $\Delta p_{tp(max)}-\Delta p_{tp(min)}$ of the variation in transpulmonary pressure and a reference value $\Delta p_{tpR}$ of the variation in transpulmonary pressure, and comprise at least first comparison means of the variation in calculated transpulmonary pressure $\Delta p_{tpC}$ with the reference interval $\Delta p_{tp(max)}-\Delta p_{tp(min)}$ or with the reference value $\Delta p_{tpR}$.

The value of the variation in calculated transpulmonary pressure $\Delta p_{tpC}$ is deemed correct if it remains within the target range $\Delta p_{tp(min)}-\Delta p_{tp(max)}$ or if it is greater than the reference value $\Delta p_{tpR}$.

Conveniently, the calculation means are also able to calculate the variation in oesophageal pressure $\Delta p_{es}$ in two different moments, respectively t1 and t2, in order to verify the efficiency of the non-invasive ventilation and the possible risks due to fatigue:

$$\Delta p_{es}=p_{es}(t1)-p_{es}(t2).$$

In the event of the probe also having a second balloon, as described above, the pumping means 4 are also associable with its second air inlet/outlet mouth for inflating/deflating the second balloon itself, in order to check the seal thereof, and the detection means can also be connected to the second balloon to detect the patient's gastric pressure $p_{ga}$.

It is emphasized that in this treatise, by the terms oesophageal pressure and gastric pressure shall also be meant all the parameters directly derivable from these such as, e.g., the pleural pressure and abdominal pressure. More particularly, the measurement of the gastric pressure makes it possible to make an estimate of abdominal pressure and therefore to obtain relevant information regarding the possible worsening of the abdominal organs thus avoiding the risk of urinary tract infections, and is in any case useful in all those cases in which it is contraindicated or in which the vesicle pressure cannot be measured.

In this second embodiment, the calculation means are able to also calculate the transdiaphragmatic pressure $p_{di}$ corresponding to the difference between the oesophageal pressure $p_{es}$ and the gastric pressure $p_{ga}$ detected in a particular moment: $p_{diC}(t)=p_{ga}(t)-p_{es}(t)$ Preferably, the processing means comprise at least a second programmable memory with at least a reference transdiaphragmatic pressure value $p_{diR}$ and comprise at least second comparison means between the calculated transdiaphragmatic pressure $p_{diC}$ and the reference transdiaphragmatic pressure $p_{diR}$. Suitably, the second programmable memory and the second calculation means may coincide with the first programmable memory and with the first comparison means mentioned above respectively.

Advantageously, in order to evaluate the presence of bilateral diaphragmatic paralysis, the calculation means are able to calculate the variation in transdiaphragmatic pressure $\Delta p_{di}$ corresponding to the difference between the variation in gastric pressure $\Delta p_{ga}$ and the variation in oesophageal pressure $\Delta p_{es}$ in two distinct moments, t1 and t2 respectively:

$$\Delta p_{di}=\Delta p_{ga}-\Delta p_{es}=(p_{ga}(t1)-p_{ga}(t2))-(p_{es}(t1)-p_{es}(t2)).$$

Conveniently, in both described embodiments, the appliance 1 comprises at least a timer operatively connected at least to the processing means 8.

More in detail, the detection means, the reading means and the calculation means are able, respectively, to detect the esophageal pressure $p_{es}$ and/or the gastric pressure $p_{ga}$, to read the pressure of the respiratory tract $p_{aw}$ and to calculate at least one of the transpulmonary pressure $p_{tp}$ the variation in transpulmonary pressure $\Delta p_{tp}$, the variation in oesophageal pressure $\Delta p_{es}$, the Compliance components of the respiratory system $C_{RS}$, chest Compliance $C_{cw}$, pulmonary Compliance $C_L$, the Elastance components of the respiratory system $E_{RS}$, chest Elastance $E_{cw}$, pulmonary Elastance $E_L$, the transdiaphragmatic pressure $p_{di}$ and the variation in transdiaphragmatic pressure $\Delta p_{di}$ at predefined and settable time intervals.

Conveniently, the appliance 1 comprises command and control means which can be selected by an operator to activate/deactivate at least one of the pumping means 4, the detection means, the reading means and the command means.

The detection and calculation of the pressures may thus occur automatically or can be commanded by the operator.

Preferably, the calculation means are able to calculate, e.g. according to the methodology described below, the optimal volume of the probe's balloons.

According to the invention, the appliance 1 also comprises graphic display means 10 operatively connected to the processing means 8 and able to display at least one of the oesophageal pressure $p_{es}$ (or the variation thereof $\Delta p_{es}$), the gastric pressure $p_{ga}$, the pressure of the respiratory tract $p_{aw}$, the transpulmonary pressure $p_{tp}$ (or the variation thereof $\Delta p_{tp}$) and the transdiaphragmatic pressure $p_{di}$. (or the variation thereof $\Delta p_{di}$), flow to the respiratory tract F, current volume (tidal) $V_T$.

Conveniently, the display means 10 are made up of an LCD touch screen.

The display means 10 may also be able to show one or more reference values $p_{esR}$, $\Delta p_{esR}$, $p_{diR}$ set in the first and/or second programmable memory.

Preferably, the display means 10 are able to display at least one graph relating to the pattern of the represented parameter as well as the relative peak and average values. More particularly, the display means 10 are the type of an LCD screen and relative graphic card.

In the preferred embodiment shown in the illustrations, the appliance 1 comprises at least an input 11 for the power supply and/or at least one rechargeable supply battery 12.

Conveniently, the appliance 1 also comprises optical and/or acoustic signalling means, able to signal the end of the calculation time interval and/or the exceeding of the reference values set by one or more of the calculated parameters.

The operation of the present invention is as follows.

Once the probe has been connected to the appliance 1, there are no leaks in the balloons by inflating and deflating them by means of the pumping means 4 and the outlet means.

After checking the tightness of the balloons, an occlusion operation can be performed of the respiratory tract in order to identify the correct positioning of the probe in the patient.

More in particular, such check is performed by means of the continuous reading and detection of the oesophageal pressure values $p_{es}$ and respiratory tract pressure values $p_{aw}$. In order to process a signal that is as clean as possible, the initially detected and read values are discarded (e.g., in the first 0.5 seconds). The oesophageal pressure values $p_{es}$ and respiratory tract pressure values $p_{aw}$ are graphically represented by the display means 10 and are used to build a regression line.

Advantageously, the operator can then proceed with the calibration of the probe, i.e., with the search phase of the optimal volume at least of the first inflatable balloon. This phase can be performed upon the specific command of the operator or automatically at predefined time intervals.

In fact, it has been shown that depending on the external volume taken by the balloon, there is a shift of the base line of the signal of the detected oesophageal pressure $p_{es}$, i.e., to the oscillatory signal of the oesophageal pressure $p_{es}$ is added a growing offset for increasing values of the external volume $V_g$ taken by the first balloon.

The calibration procedure is performed as follows:
inflation of the balloon to a certain external volume $V_g$, between a minimum volume and a maximum volume;
reading and recording, once the desired volume has been reached and for a specific time period, of the values of oesophageal pressure $p_{es}$, of respiratory tract pressure $p_{aw}$, of volume V inhaled or exhaled by the patient and of the air flow F inhaled or exhaled by the patient;
elimination of the values recorded in the first part of the above time period, so as to obtain a more stable path;
repetition of these phases for each intermediate volume $V_g$.

The recorded data are processed as follows:
a) Calculation of minimum oesophageal pressure $p_{es\ min}$.
To calculate the minimum oesophageal pressure $p_{es\ min}$ proceed as follows:
calculate the filtered oesophageal pressure $p_{es\ F}$:
$p_{es\ F}$=mobile average of $p_{es}$ with step 160 ms.
calculate the minimum value of $p_{es\ F}$ for each breath:
$p_{es\ F\ min}$ within the individual complete acts (from an opening of the inhalation valve to the next) in the period of 20 s analyzed for each volume $V_g$;
calculate the maximum excursion of the $p_{es\ F\ min}$ in 20 seconds, which should not exceed 2 cm $H_2O$:

$$\text{Max}(p_{es\ F\ min})-\text{min}(p_{es\ F\ min}) \leq 2\ cmH_2O$$

If the ratio is not satisfied, the analysis of volume $V_{g\ (i)}$ is repeated; in case of its not being satisfied again, a window appears asking if the patient is truly passive;
calculate the mean value between the minimum of $p_{es\ F}$ in the 20 seconds analyzed: mean $p_{es\ F\ min\ (i)}$.
b) Identification of plateau and slope plateau.
Perform a linear regression on all the triplets $T_i$ thus identified:

$$T_i = \{(\text{mean } p_{es\ F\ min\ (i)}, V_{g\ (i)}), (\text{mean } p_{es\ F\ min\ (i+1)}, V_{g\ (i+1)}), (\text{mean } p_{es\ F\ min\ (i+2)}, V_{g\ (i+2)})\}$$

where $V_{g\ (i)}$, $V_{g\ (i+1)}$, $V_{g\ (i+2)}$ are all possible volumes (0.5 and 1.5 the half volumes considered initially) with $i \in [1.7]$:

| $V_{g(1)}$ | $V_{g(2)}$ | $V_{g(3)}$ | $V_{g(4)}$ | $V_{g(5)}$ | $V_{g(6)}$ | $V_{g(7)}$ | $V_{g(8)}$ | $V_{g(9)}$ | $V_{g(10)}$ |
|---|---|---|---|---|---|---|---|---|---|
| 0 ml | 0.5 ml | 1 ml | 1.5 ml | 2 ml | 3 ml | 4 ml | 5 ml | 6 ml | 7 ml |
| | | | 0 ml-0.5 ml-1 ml | | | | | | |
| | | | 0.5 ml-1 ml-1.5 ml | | | | | | |
| | | | 1 ml-1.5 ml-2 ml | | | | | | |
| | | | 1.5 ml-2 ml-3 ml | | | | | | |
| | | | 2 ml-3 ml-4 ml | | | | | | |
| | | | 3 ml-4 ml-5 ml | | | | | | |
| | | | 4 ml-5 ml-6 ml | | | | | | |
| | | | 5 ml-6 ml-7 ml | | | | | | |

Calculate the slope $\text{SlopeTripletta}_i$ as slope of the triplet $T_i$ and determine which triplet has the minimum slope $\text{SlopeTriplettaMin}$:

$$\text{SlopeTriplettaMin} = \text{Min}(\text{SlopeTripletta}_i)$$

All the volumes $V_{g\ (i)}$ of the triplets Ti are accepted as falling within the plateau which have a slope of no more than 125% of the minimum one:

$$V_{g\ (i)}, V_{g\ (i+1)}, V_{g\ (i+2)} \in \text{Plateau} \Leftrightarrow \text{SlopeTripletta}_i \leq 1,25\ \text{SlopeTriplettaMin}$$

If there are not at least 4 volumes $V_{g(i)}$ belonging to the Plateau then the above steps are performed a second time using the adjacent volumes X,5 within the triplet with minimum slope. Example triplet with minimum slope 3-4-5: the half volumes 2.5 3.5 4.5 and 5.5 are evaluated.

The Plateau is defined by an interval $[V_{g\ MIN}, V_{g\ MAX}]$;
calculate the slope of the plateau (SLOPEPLAT) by linear regression of mean $P_{ESF\ min}$ on $V_g$ for the $V_g$ belonging to the plateau (the $V_g$ belonging to the triplet with minimum slope and to triplets with slope <1.25* SLOPETRIPLETTAMIN).

The regression of (mean$P_{es\ F\ min\ (i)}$, $V_{g\ (i)}$) is performed for each $V_{g\ (i)} \in$ Plateau.

c) Identification of the best volume from among those belonging to the plateau.

The following are calculated:
the SLOPECHEST slope by linear regression;
the $R^2$ of the ratio $p_{es}$–Vol (using the unfiltered values);
the median of the $R^2$, defined as $R^2_{MED}$.

The best volume $V_{g\ AUTO}$ will be the one that satisfies the following conditions:

The ratio $p_{es}$–Vol of the $V_{g\ (i)}$ volume has an $R^2$ higher than that of the median $$R^2(V_{g\ (i)}) > R^2_{MED}$$

The slope $p_{es}$–Vol for the volume $V_{g\ (i)}$ is the highest among those of the plateau volumes:

$$\text{SLOPECHEST}(V_{g\ AUTO}) > \text{SLOPECHEST}(V_{g\ (i)}) \text{ for each } V_{g\ (i)} \in \text{Plateau}$$

where Plateau=$[V_{g\ MIN}, V_{g\ MAX}]$

At the end of the calibration the doctor is asked whether he/she wants to:
Accept the $V_{g\ AUTO}$ suggested to him/her;
Use a $V_g$ value of the Plateau or an intermediate value between two of these (adjustable in steps of 0.1 ml);
Use a $V_g$ value, outside the Plateau. In this case, the doctor is informed he/she is out of the suggested range;
Not do anything, in which case after 30 seconds the balloon is inflated to the volume $V_{g\ AUTO}$.

d) Calculation of the calibrated $p_{es}$.
Display the $p_{es}$ in real time;
Calculate the Tidal Volume of each act as:

$$V_{T\ atto} = \text{Vol}_{MAX} - \text{Vol}_{min}$$

Where $\text{Vol}_{min}$ is the volume that the appliance 1 detects at each end of cycle, just before being reset.

In the period between two changes of state from inhalation to exhalation (=between two recognitions of openings of the inhalation valve);
run the mean of the $V_T$ values obtained during the respiratory cycles included in the 20 seconds of analysis of $V_{g\ (i)}$:

$$V_T = \text{mean}(V_T\ \text{act})$$

for all $V_T$ act considered in the 20 sec of analysis;
calculate the minimum and maximum calibrated oesophageal pressure values, as well as its excursion, as:

$$p_{es\ min\ CALIBRATA} = \text{mean}\ p_{es\ F\ min\ (i)} - \text{SLOPEPLAT}*(V_{g\ (i)} - V_{g\ MIN})$$

$$p_{es\ MAX\ CALIBRATA} = p_{es\ min\ CALIBRATA} + \Delta p_{es}$$

$$\Delta p_{es} = \text{SLOPEPLAT}*V_T$$

An indication of the quality of the oesophageal pressure signal is graphically displayed based on the $R^2$ of the ratio ($P_{es}$–Vol)

After therefore terminating the calibration step, which remains in any case at the discretion of the operator, it is possible to proceed with measurements.

The operator, by means of the command and control means, can choose which type of measurement to make from among those available, or the variation in transpulmonary pressure $\Delta p_{tp}$ at the end of inhalation and exhalation phases, the variation in the oesophageal pressure $\Delta p_{es}$, the transdiaphragmatic pressure $p_{di}$ or its variation $\Delta p_{di}$.

Conveniently, before each new measurement, the processing means check the time which has elapsed since the last measurement taken and if this time interval is greater than a predefined value (e.g., one hour), these intervene by means of the pumping means 4 and the air outlet means to perform the operation of deflation/reinflation of the relative balloon, so as to return it to the desired volume of inflation $V_g$.

The measured values and the related graphs are displayed by the display means 10 so as to provide an intuitive indication which is easy for the healthcare operator to read.

In has in practice been ascertained how the described invention achieves the proposed objects and in particular the fact is underlined that it allows the healthcare operator to use the known type of probes in an easy and fast way, whether these have one or two balloons.

More in detail, the appliance according to the invention enables the automatic detection of all parameters of interest for the health operator and is simple and intuitive to use.

What is claimed is:

1. Appliance (1) for enteral nutrition by means of a probe of the type comprising a tubular element of elongated shape and substantially flexible which defines a feeding channel open at the extremities for the introduction of nutritional substances in the stomach of a patient and which comprises at least a first inflatable balloon for detecting the pressure inside the oesophagus of a patient, said tubular element comprising at least a first inlet/outlet mouth for the air in/from said first balloon, wherein said appliance (1) comprises:

at least a pneumatic circuit (3) having pumping means (4) associable at least with said first inlet/outlet mouth for inflating/deflating said first balloon, where said pumping means (4) are the type of a syringe pump;

processing means (8) comprising:
 detection means which can be connected at inlet at least to said first balloon to detect at least the patient's oesophageal pressure ($p_{es}$);
 reading means of the pressure of the respiratory tract ($p_{aw}$) which can be connected at inlet to an external detection device;
 calculation means operatively connected at inlet to said detection means and to said reading means and configured to calculate at least the transpulmonary pressure ($p_{tp}$) corresponding to the difference between the pressure of the respiratory tract ($p_{aw}$) read and the oesophageal pressure ($p_{es}$) detected in a particular moment, said calculation means are configured to calculate a variation in transpulmonary pressure ($\Delta p_{tpC}$) in two different moments ($t_1$, $t_2$);
 at least a first programmable memory with at least one of a reference interval ($\Delta p_{tpmin}$, $\Delta p_{tpmax}$) and a reference value ($\Delta p_{tpR}$) of the variation in transpulmonary pressure ($\Delta p_{tp}$), wherein the processing means (8) are configured to compare the variation in calculated transpulmonary pressure ($\Delta p_{tpC}$) with said reference interval ($\Delta p_{tpmin}$, $\Delta p_{tpmax}$) or with said reference value ($\Delta p_{tpR}$);

graphic display means (10) operatively connected to said processing means (8) and able to display at least one of said oesophageal pressure ($p_{es}$), said pressure of the respiratory tract ($p_{aw}$) and said transpulmonary pressure ($p_{tp}$).

2. An appliance (1) according to claim 1, comprising at least an Ethernet port.

3. An appliance (1) according to claim 1, wherein said calculation means are configured to calculate the variation in oesophageal pressure ($\Delta p_{es}$) in two different moments.

4. An appliance (1) according to claim 1, wherein said probe comprises at least a second inflatable balloon for detecting the pressure in the patient's stomach, said tubular element comprising at least a second inlet/outlet mouth for the air in/from said second balloon, characterised by the fact that said pumping means (4) are associable at least with said second inlet/outlet mouth for inflating/deflating said second balloon, that said detection means can be connected at inlet to said second balloon to detect at least the patient's gastric pressure ($p_{ga}$) and that said display means (10) are able to display at least said gastric pressure ($p_{ga}$).

5. An appliance (1) according claim 4, wherein said calculation means are able to calculate the transdiaphragmatic pressure ($p_{diC}$) corresponding to the difference between the oesophageal pressure ($p_{es}$) and the gastric pressure ($p_{ga}$) detected in a particular moment (t).

6. An appliance (1) according to claim 5, wherein said processing means (8) comprise at least a second programmable memory with at least a reference transdiaphragmatic pressure value ($p_{diR}$) and the processing means (8) are configured to compare said calculated transdiaphragmatic pressure ($p_{diC}$) and said reference transdiaphragmatic pressure ($p_{diR}$).

7. An appliance (1) according to claim 4, wherein said calculation means are configured to calculate the variation in transdiaphragmatic pressure ($\Delta p_{di}$) corresponding to the difference between the variation in gastric pressure ($\Delta p_{ga}$) and the variation in oesophageal pressure ($\Delta p_{es}$) in two distinct moments ($t_1, t_2$).

8. An appliance (1) according claim 4, comprising at least a timer operatively connected to said processing means (8), said detection means, said reading means and said calculation means being able respectively, to detect the esophageal pressure ($p_{es}$) and/or the gastric pressure ($p_{ga}$), to read the pressure of the respiratory tract ($p_{aw}$) and to calculate at least one of the transpulmonary pressure ($p_{tp}$), the variation in transpulmonary pressure ($\Delta p_{tp}$), the variation in oesophageal pressure ($\Delta p_{es}$), the transdiaphragmatic pressure ($p_{di}$) and the variation in transdiaphragmatic pressure ($\Delta p_{di}$) at predefined time intervals.

9. An appliance (1) according to claim 4, wherein said pneumatic circuit (3) comprises at least an air inlet/outlet gap (5) having a connection of the Luer-lock type associable with the air inlet/outlet mouth of one of said balloons.

10. An appliance (1) according to claim 1, wherein said calculation means are configured to calculate an optimal volume of said balloons.

11. An appliance (1) according to claim 1, comprising command and control means which can be selected by an operator to activate/deactivate at least one of said pumping means (4), said detection means, said reading means and said calculation means.

12. An appliance (1) according to claim 1, comprising at least one rechargeable supply battery (12).

13. An appliance (1) according to claim 1, wherein said display means (10) are of the touch-screen type.

14. Appliance (1) according to claim 1, comprising optical and/or acoustic signalling means operatively connected to said processing means (8).

* * * * *